United States Patent [19]

Buard et al.

[11] Patent Number: 5,716,786
[45] Date of Patent: Feb. 10, 1998

[54] VNTR PROBES AND METHODS OF USING THEREOF

[75] Inventors: Jerome Buard, Paris; Dominique Gauguier, St Mande; Gilles Vergnaud, Paris, all of France

[73] Assignee: L'Etat Francais, represente par le Delegue Ministeriel pour l'Armement, Armees, France

[21] Appl. No.: 690,129

[22] Filed: Jul. 31, 1996

Related U.S. Application Data

[62] Division of Ser. No. 331,910, Oct. 31, 1994, Pat. No. 5,573,912.

[30] Foreign Application Priority Data

Oct. 29, 1993 [FR] France .................. 93 12923

[51] Int. Cl.$^6$ .................. C12Q 1/68; C07H 21/04; C07H 21/02
[52] U.S. Cl. .................. 435/6; 435/21; 536/23.1; 536/24.3; 536/24.31; 935/77; 935/78
[58] Field of Search .................. 435/6, 21; 536/23.1, 536/24.3, 24.31; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,963,663 | 10/1990 | White et al. | 536/24.31 |
| 5,032,501 | 7/1991 | Milner | 435/6 |
| 5,075,217 | 12/1991 | Weber | 435/6 |
| 5,097,024 | 3/1992 | Hodes et al. | 536/27 |
| 5,273,878 | 12/1993 | Groffen et al. | 435/6 |
| 5,364,759 | 11/1994 | Caskey et al. | 435/6 |
| 5,369,004 | 11/1994 | Polymeropoulos et al. | 435/6 |
| 5,378,602 | 1/1995 | Polymeropoulos et al. | 435/6 |
| 5,411,859 | 5/1995 | White et al. | 435/6 |
| 5,427,932 | 6/1995 | Weier et al. | 435/6 |
| 5,556,955 | 9/1996 | Vergnaud | 536/24.31 |

FOREIGN PATENT DOCUMENTS

| | | |
|---|---|---|
| 0 201 184 | 12/1986 | European Pat. Off. |
| 2 680 520 | 2/1993 | France |

OTHER PUBLICATIONS

Vergnaud, Gilles et al., "Detection of Single and Multiple Polymorphic Loci by Synthetic Tandem Repeats of Short Oligonucleotides," *Electrophoresis*, 12, pp. 134–140 (1991).

Jeffreys, Alec. J., "Highly Variabel Minisatellites and DNA Fingerprints," *Biochemical Society Transactions*, vol. 15, Twenty–Third Colworth Medal Lecture, Sep. 1986, pp. 309–317.

Wong, Z. et al., "Characterization of a Panel of Highly Variable Minisatellites Cloned From Human DNA," *Ann. Hum. Genet.*, 51, 269–288, (1987).

Zishcler, Hnas et al., "Dissecting $(CAC)_5/(GTG)_5$ Multilocus Fingerprints From Man into Individual Locus–Specific, Hypervariable Components," *Genomics* 13, 983–990 (1992).

Armour, John A. L. et al., "Systematic Cloning of Human Minisatellites from Ordered Array Charomid Libraries," *Genomics* 8, 501–512 (1990).

Feinberg, Andrew P. et al., "A Technique for Radiolabeling DNA Restriction Endonuclease Fragments to High Specific Activity," *Analytical Biochemistry*, 132, 6–13 (1983).

Litt, M. et al., "A Highly Polymorphic Locus in Human DNA Revealed by Cosmid–Derived Probes," *Proc. Natl. Acad. Sci.*, vol. 82, Sep. 1985, pp. 6206–6210.

Vergnaud, G. et al., "Detection, Cloning, and Distribution of Minisatellites in Some Mammalian Genomes," *Experimentia Supplementum (Basel)*, DNA Fingerprinting: State of the Science; Ed. by S.D.J. Pena et al., vol. 67, pp. 47–57, (1993).

Nakamura et al., "Variable Number of Tandem Repeat (VNTR) Markers for Human Gene Mapping," *Science*, vol. 235, pp. 1616–1622, (1987).

Stratagene, Product Catalog 1991, p. 38 and p. 119.

Ali et al., "Enzymatic Synthesis of DNA Probes Complementary to a Human Variable Number Tandem Repeat Locus", *Analytical Biochem*, 179, pp. 280–283, (1989).

Nakamura et al., "New Approach for Isolation of VNTR Markers", *Am. J. Hum. Genet*, vol. 43, pp. 854–859 (1988).

Vergnaud et al., "The Use of Synthetic Tandem Repeats to Isolate New VNTR Loci: Cloning of a Human Hypermutable Sequence", *Genomics*, vol. 11, pp. 135–144, (1991).

*Primary Examiner*—W. Gary Jones
*Assistant Examiner*—Paul B. Tran
*Attorney, Agent, or Firm*—Oliff & Berridge, P.L.C.

[57] ABSTRACT

According to the process of the invention, sets of restriction fragments from the DNA of an individual are prepared, these restriction fragments being separated by size. Probes are prepared by enzymatic hydrolysis of DNA from a genome bank of the species to which this individual belongs, separation of the fragments obtained as a function of their size, labeling these probes and placing them in contact, under hybridization conditions, with the aforementioned sets of restriction fragments. Finally, selection is made of the probes (capable of hybridizing with said set of restriction fragments) which do not give hybridization profiles identical to those obtained with known probes recognizing variable number tandem repeat regions. Applications for the probes thus obtained include, particularly, processes for identifying an individual, consanguinity testing, and investigating the origin of a seed.

14 Claims, No Drawings

VNTR PROBES AND METHODS OF USING THEREOF

This application is a division of application Ser. No. 08/331,910, filed Oct. 31, 1994, now U.S. Pat. No. 5,573,912.

BACKGROUND OF THE INVENTION

The invention relates to a process for selecting and/or obtaining nucleic acid probes capable of detecting new variable number tandem repeat regions present in the genomes of higher eucaryotes, probes obtainable in this way, and their applications.

With the development of molecular biology and its application to daily life, circumstances requiring genetic identification are increasingly frequent. Among these we may cite identification of an individual, particularly in police investigations or paternity testing, identification of a cell line, or checking the origin of a human, animal, or plant seed.

However, in view of the complexity of the genomes in higher eucaryotes, a complete genome analysis for a given individual cannot be contemplated at the present time.

Hence it is necessary to resort to using markers of this genetic identity.

It has recently been shown that useful markers designated "variable number tandem repeat regions" (VNTR regions or VNTRs for short) exist in the genomes of higher eucaryotes; these regions are also known as "hypervariable regions" or "minisatellite regions."

Each locus corresponding to a VNTR is composed of a series of tandem repeat nucleotides of which the number of repeats varies from one individual to another. However, not all the repeated sequences are fully identical. Nonetheless, for a given species, a given locus repeats largely identically.

The various VNTRs of a given individual are dispersed throughout the genome and are distinguished from each other, not only by the sequence of the repeated motif, but also by the number of repetitions of their own motif.

Of the methods for detecting these regions used to date, one may cite the screening of a bank using nucleotide probes with natural tandem repeats (Wong et al., *Ann. Hum. Genet.*, 51, 269–288, 1987) or synthetic probes (Zischler et al., *Genomics*, 13, 983–990, 1992). One may also cite the method described in French patent application FR 91.10516, consisting of screening a bank enriched with VNTRs using nucleotide probes with artificial tandem repeats, as well as the method consisting of a systematic search in a genomic bank (Armour et al., *Genomics*, 8, 501–512).

However, these methods have proved inadequate in that, thus far, they have enabled documentation of only about 10% of the estimated number of VNTRs for the human species.

SUMMARY OF THE INVENTION

It has now been discovered that, surprisingly, by using fragments of genomic DNA obtained after DNA hydrolysis with certain restriction enzymes and selected by size, it is possible to obtain easily new probes capable of new VNTRs. The present invention relates to a method for selecting and/or obtaining nucleic acid probes capable of detecting new VNTRs in the genome of a given species. According to the process of the invention, sets of restriction fragments from the DNA of an individual are prepared, these restriction fragments being separated by size.

Probes are prepared by enzymatic hydrolysis of DNA from a genome bank of the species to which this individual belongs, separation of the fragments obtained as a function of their size, labeling these probes and placing them in contact, under hybridization conditions, with the aforementioned sets of restriction fragments.

Finally, selection is made of the probes (capable of hybridizing with said set of restriction fragments) which do not give hybridization profiles identical to those obtained with known probes and recognizing variable number tandem repeat regions.

Applications for the probes thus obtained include, particularly, processes for identifying an individual, consanguinity testing, and investigating the origin of a seed.

DESCRIPTION OF THE INVENTION

In the present application, "probe" is understood to be any single-stranded nucleotide sequence that may match with a VNTR according to the well-known purine-pyrimidine matching properties of complementary nucleic acid strands in DNA-DNA, DNA-RNA, and RNA-RNA duplexes. This matching process is accomplished by the establishment of hydrogen bonds between the adenosine-thymine (A-T) and guanosine-cytosine (G-C) bases of double-stranded DNA; adenosine-uracil (A-U) base pairs may also form by hydrogen bonding in the DNA-RNA or RNA-RNA duplexes. Matching of nucleic acid strands to identify a nucleic acid molecule is usually called "nucleic acid hybridization" or simply "hybridization."

"New VNTR" is understood to be a genome region not yet identified as such, for which no specific probe is known from the literature.

The present invention relates to a method for selecting and/or obtaining nucleic acid probes capable of detecting new VNTRs in the genome of a given species, characterized in that:

a) a set of restriction fragments is prepared from the DNA of an individual of said species, said set being obtained, in a manner known of itself, by hydrolysis of a sample containing at least part of the genomic DNA of said individual, with the aid of at least one restriction enzyme cutting at an essentially constant distance from the site which it recognizes, after which the restriction fragments are separated by size, b) the steps in paragraph a) above are repeated on similar samples of genomic DNA from the same individual to obtain a plurality of such restriction fragment sets, c) in addition, probes are prepared by enzymatic hydrolysis of DNA of a genomic bank of said species with the aid of at least one restriction enzyme cutting at an essentially constant distance from the site that it recognizes, then separation by size of the restriction fragments obtained, selection of fragments longer than 1.5 kb, and labeling said fragments by known methods, the thus obtained, labeled fragments of the same size constituting a probe, d) each of the probes thus obtained is placed in contact, under hybridization conditions, with one of the sets of restriction fragments obtained in paragraph a) or b) above, e) a selection is made of the probes which, under these conditions, are capable of hybridization with restriction fragments, of at least a given length, from the set of fragments with which the probe in question was placed in contact, f) in addition, a selection is made of the probes which, with a set of restriction fragments obtained as in paragraph a) of DNA from an individual of the same species, do not give hybridization profiles identical to those obtained, with known probes recognizing VNTRs, on sets of restriction fragments obtained in a similar manner and coming from the same individual, g) and, if desired, a nucleic acid probe including at least part of the sequence of the probes thus selected may be sequenced and/or synthesized and/or labeled with a tracer by known methods.

Of course it is possible, by using known methods, including those of paragraph g) above, to confirm that the nucleic acid probe obtained by the method of the invention does indeed recognize a VNTR. Further on in the specification, other methods for obtaining such a confirmation will be indicated.

According to one embodiment of the method according to the invention, it includes after step e) two additional steps d') and e') consisting of repeating steps d) then e), but with sets of restriction fragments obtained from the DNA of an individual other than the individual from which the DNA used in steps a) and b) was obtained. Of the probes capable of hybridizing with a set of restriction fragments coming from another individual, after step e'), those which give a hybridization profile different to that obtained with the fragments prepared in step a) or b) are selected.

The restriction enzyme used in the method according to the invention is preferably an enzyme which recognizes a short and hence frequent sequence in the genome and has a restriction site at a constant or near-constant distance from the recognized site. Of the enzymes possessing the required properties, one may cite in particular class II enzymes, namely those which cut at a specific site near the recognized site or included in the recognized site, and class III enzymes, which cut at a nonspecific site but at a constant or near-constant distance, on the order of 20 bases, from the recognized site. Of the usable enzymes, one may cite, for example, Alu I, Hae III, and Hinf I.

According to a preferred embodiment of the method according to the invention, enzymatic hydrolysis is accomplished with the aid of two enzymes chosen from the aforementioned enzymes.

Separation of restriction fragments as a function of size may be accomplished by any known method, for example, by electrophoresis.

Of course, "fragment size" is understood to be fragment length, expressed as the number of nucleotides. The fragments are considered to be of the same size if, by using the separation process employed, said fragments are not separated. Thus, for example, when 1% agarose gel electrophoresis is used as the separation process, fragments are considered to be of the same size if their lengths differ by no more than approximately 50 to 100 bases.

"Genomic bank" designates any storage mode for the genome of an individual, which bank may be partial or total, namely containing all or part of said genome. The genome banks used are notably in the form of microorganisms into which, according to known methods, fragments of the genome or part of the genome to be stored are inserted. Among microorganisms in current use, bacteria, viruses, and yeasts in particular may be cited. The genome fragments to be stored are inserted directly into the genome of the recipient microorganism or are in an independent form, such as a plasmid. The use of these banks allows, through preculture of the microorganisms, the number of copies of the genome or the part of the genome to be studied to be easily increased. The sought-after genetic material is then extracted by known methods.

In one particular embodiment, the bank used to prepare probes according to the method of the invention is a human genome bank, particularly a cosmid bank. Of the human genome banks in cosmid form, one may cite in particular the banks sold under the number "HL 1145y" by the Clontech Company or under the number "951202" by the Stratagene Cloning System Company, or that made from the Supercos I vector, number "961200" with the encapsidation lysate known as "Gigapack II" sold by the Stratagene Cloning System Company.

According to another embodiment, the bank used is a rat genome bank such as that sold under number "RL1032m" by the Clontech Company.

The bank used may also be a chicken genome bank such as that sold under number "951401" by the Stratagene Cloning System Company.

The probes used in the method according to the invention may be labeled by any marker in traditional use.

They may in particular be labeled using a radioactive tracer such as $^{32}P$, $^{33}S$, $^{125}H$, and $^{14}C$. Radioactive labeling may be accomplished by known methods.

The nucleotide sequences may in particular be labeled at the 3' end by adding one or more deoxyribonucleotides or ribonucleotides, or a nucleotide analog such as a dideoxynucleotide, labeled at the alpha position by $^{32}P$ in the presence of deoxynucleotidyl terminal transferase; the nucleotide sequences can also be labeled at the 5' end with the aid of a kinase, for example T4 polynucleotide kinase; in this case, the radioactive phosphate is transferred from a nucleotide labeled at the gamma position to the polynucleotides. The nucleotide sequences can also be labeled at each end by adding any radiolabeled sequence in the presence of a ligase.

The probes can also be labeled by random priming or, during their chemical synthesis, by incorporation of one or more radioactive ribonucleotides or deoxyribonucleotides.

The hybridization detection method will depend on the radioactive label used and may be based on autoradiography, liquid scintillation, gamma radiation counting, or any technique allowing the radiation given off by the radioactive label to be detected.

Non-radioactive labeling may also be used, in a manner known of itself, for example by combining with the nucleotide sequences substances that have immunologic properties, such as an antigen or a hapten, or have a specific affinity for certain reagents, such as a ligand, or have properties allowing completion of enzymatic reactions such as an enzyme or an enzyme substrate. The nucleotide sequences can be labeled by random priming or, during their chemical synthesis, by incorporating one or more non-radioactively labeled ribonucleotides or deoxyribonucleotides. Non-radioactive labeling can also be accomplished by incorporation into the 3' end of one or more deoxyribonucleotides or ribonucleotides, or a nucleotide analog such as a didesoxynucleotide including one of these groups. Labeling can also be done directly by chemical modification of the oligonucleotide, such as photobiotinylation or sulfonation, or by fixation of DNA-specific dyes which are fluorescent when fixed such as the dimers of oxazole or thiazole orange. It can also be accomplished by addition of tracer molecules at the 3' or 5' end by chemical reaction after synthesis; also the nucleotide sequences can be labeled at each end by adding, in the presence of a ligase, any sequence including tracer molecules. The method of hybridization detection and development, carried out in a manner known of itself, will obviously depend on the non-radioactive label used.

The hybridization conditions of the method according to the invention are preferably discriminant conditions, thus allowing the specificity of said hybridization to be increased.

Among these conditions, one may cite in particular a temperature of between 60° and 75° C. and in particular between 65° C. and 70° C., and an ion concentration between 0.3 and 1.2M and preferably equal to 0.9M of $Na^+$ ions. The hybridization step proper is followed by several washings at 65° C. in a medium with a lower ion concentration, in particular between 0.015 and 0.15M of $Na^+$.

Using the method according to the invention, a hybridization profile is obtained for each set of fragments. When different hybridization profiles are obtained from sets of restriction fragments from one and the same individual placed in contact both with the probe obtained by the method and with known probes, it may be concluded that the probe obtained is new: namely, it is a probe able to identify a not-yet-known VNTR.

When different hybridization profiles are obtained from sets of restriction fragments from different individuals, placed in contact with one and the same probe, this confirms the variability of the VNTR detected. For this reason, the two individuals tested should preferably be unrelated in order to decrease the probability of revealing identical alleles.

When the hybridization profiles obtained are identical, namely when hybridization is observed on fragments of the same size, one may not conclude that the region detected lacks variability, as two hypotheses may then be considered: either the probe used is indeed detecting a region that does not meet the definition of a VNTR, or the probe used is detecting a VNTR but the two individuals tested have identical alleles for the same region. To conclude, one may then analyze a set of restriction fragments coming from the DNA of a third individual obtained in the same manner as for the sets of fragments from the first two individuals, and thus determine whether the region tested is variable or not.

The present invention also relates to probes detecting new VNTRs that may be obtained by the method according to the invention.

Among the probes according to the invention, one may cite in particular:

the new probes obtained according to the method of the invention from human genome banks sold under reference number "HL 1145y" by the Clontech Company or under reference number "951202" by the Stratagene Cloning System Company, or that made from the Supercos I vector, reference number "961200", with the encapsidation lysate known as "Gigapack II" sold by the Stratagene Cloning System Company, and in particular the probes described in the following examples:

the new probes obtained according to the method of the invention from a rat genome bank sold under the reference number "RL 1032m" by the Clontech Company;

the new probes obtained according to the method of the invention from the chicken genome bank sold under the reference number "951401" by the Stratagene Cloning System Company.

In particular, the present invention relates to new probes characterized by their containing a sequence of at least 40 nucleotides chosen from the human genome sequence contained in one of the following cultures, deposited with Collection Nationale des Cultures Microorganismes (CNCM) at the Institut Pasteur on Jul. 30, 1993 under numbers:

I-1343 for cosmid 159E5 containing locus D1S339,

I-1344 for cosmid 32A8 containing locus D11S1000,

I-1345 for cosmid 33F4 containing locus D8S358,

I-1346 for cosmid 51A11 containing locus D17S885, and

I-1347 for cosmid 151A7 containing locus D13S324, which probes are designated respectively by references "CEB88", "CEB41", "CEB42", "CEB49", and "CEB69."

The present invention also relates to synthetic or semi-synthetic polynucleotide probes equivalent to the new probes obtained by the method according to the invention (i.e. probes with the same hybridization properties). Modified probes may also be prepared, particularly ribonucleic acid probes or deoxyribonucleic acid probes in which one of the four bases is modified, and in particular, replaced by a base such as, for example, inosine.

The invention thus extends to any polynucleotide probe distinguished from a probe obtained directly by the method according to the invention only by the addition and/or deletion and/or substitution of one or more nucleotides while retaining the same properties of hybridization with the VNTR recognized by said probe directly obtained by said process. In particular, one may cite polynucleotides whose sequence is identical to that of a part of the probe initially obtained, but which is lacking the region or regions bordering the VNTR.

"Border region" is understood to be the 200 nucleotides located on either side of the VNTR proper.

It is also of course possible to multiply by amplification, by known methods, the probes capable of detecting VNTRs obtained by the method of the invention or the equivalent probes as defined above. The amplification method consists, for example, of using a first primer matching at least part of a sequence bordering the hypervariable region, such as one that may be obtained from cosmids, and a second primer containing at least part of the sequence of the other border region, then implementing an enzymatic extension process using DNA-polymerase, followed by a denaturing process, then repeating the hybridization-extension-denaturing cycle, this method being known as PCR (U.S. Pat. Nos. 4,683,195; 4,683,202; and 4,800,159, and EP No. 0 201 184) to obtain a sufficient number of copies of probes according to the invention.

The present invention also relates to the use of the probes described above.

The present invention relates in particular to the use of the probes as defined previously in consanguinity searches, screening for tumoral or hereditary diseases, or identification of a biological specimen.

According to one particular embodiment, the probes as defined above are used, particularly for human beings, in a consanguinity search method, comprising:

a first step in which said labeled probe or probes is/are each placed in contact, under hybridization conditions, with a set of restriction fragments obtained by hydrolyzing a sample of genomic DNA from a tested individual with the aid of at least one restriction enzyme cutting at an essentially constant distance from the site it recognizes, followed by separation of said fragments as a function of size;

a second step in which said labeled probe or probes is/are each placed in contact, under hybridization conditions, with a set of restriction fragments obtained by hydrolyzing a sample of genomic DNA from a second individual, whose consanguinity with said tested individual is to be determined, using the restriction enzyme or enzymes used in the first step, which fragments are also separated by size; and a third step in which the sizes of the fragments hybridizing with said probe or probes are compared for the two individuals, it being understood that there is a presumption of consanguinity when the size of the fragments hybridizing with said probe or probes is identical.

One may conclude that consanguinity exists between two individuals when a sufficiently representative number of fragments hybridizing with probes obtained according to the invention have the same size.

In particular, the process described above may be used for consanguinity testing by the method described by Alec Jeffreys ("highly variable minisatellites and DNA fingerprints", *Biochemical Society Transactions*, Vol. 15, pp. 309–317, 1987) or by Wong et al., ("Characterization of a panel of highly variable minisatellites cloned from Human DNA", *Ann. Hum. Genet.*, 51, pp. 269–288, 1987).

This process may of course also be applied to verifying the origin of any animal or plant seed.

The probes according to the invention can also be used for a process for screening genetic abnormalities associated with certain cancers or hereditary diseases.

The cancer-forming process is sometimes accompanied by general genetic instability bringing about mutations and/or losses of chromosome fragments, particularly fragments carrying antitumor genes. This general instability may result in a change in the number of pattern repeats of a VNTR or even in the deletion of a VNTR.

Hence the present invention relates to the use of probes as defined above in a screening process for tumoral diseases, characterized by comprising:

a first step in which said labeled probe or probes is/are each placed in contact, under hybridization conditions, with a set of restriction fragments obtained by hydrolyzing a sample of genomic DNA from test cells of an individual with the aid of at least one restriction enzyme cutting at an essentially constant distance from the site it recognizes, followed by separation of said fragments as a function of size;

a second step in which said labeled probe or probes is/are each placed in contact, under hybridization conditions, with a second set of restriction fragments obtained by hydrolyzing a sample of genomic DNA from normal cells of the same individual, using the restriction enzyme or enzymes used in the first step, which fragments are also separated by size; and a third step in which a comparison is made, in both categories of cells, of the number and size of the fragments hybridizing with said probe or probes, it being understood that there is a presumption of tumoral disease when the number or size of fragments hybridizing with said probe(s) differs.

The probes as defined according to the invention can also be used in a process of screening for hereditary diseases in which losses of chromosome fragments carrying VNTR are observed, for example telomeric microdeletions associated with mental retardation.

The invention thus relates to the use of probes as defined above in a process of screening for hereditary diseases characterized by comprising:

a first step in which, under hybridization conditions, said labeled probe or probes is/are each placed in contact with a set of restriction fragments obtained by hydrolyzing a sample of genomic DNA from a first individual to be tested, with the aid of at least one restriction enzyme cutting at an essentially constant distance from the site that it recognizes, said fragments then being separated by size, a second step in which, under hybridization conditions, said labeled probe or probes is/are each placed in contact with a second set of restriction fragments obtained by hydrolyzing a sample of genomic DNA from a healthy individual, with the aid of the restriction enzyme or enzymes used previously, said fragments also being separated by size, and a third step in which the number of fragments hybridizing with said probe or probes in the two individuals is compared, it being understood that there is a presumption of the existence of hereditary disease when the number of fragments hybridizing with said probe(s) differs.

Here, "healthy individual" is understood to be an individual who does not have the suspected hereditary disease.

The probes according to the invention can also be used to determine whether a biological specimen comes from a given individual to be tested. This application is particularly useful in police investigations to determine whether a biological specimen indeed comes from an individual under suspicion.

According to this particular embodiment, the present invention thus relates to the use of probes as defined above in a process of identification of a biological specimen by comparison with the DNA of a test individual, characterized by comprising:

a first step in which, under hybridization conditions, said labeled probe or probes is/are each placed in contact with a set of restriction fragments obtained by hydrolyzing the DNA of said biological specimen, with the aid of at least one restriction enzyme cutting at an essentially constant distance from the site that it recognizes, followed by separation of said fragments as a function of size, a second step in which, under hybridization conditions, said labeled probe or probes is/are each placed in contact with a second set of restriction fragments obtained by hydrolyzing a sample of genomic DNA from the individual tested, with the aid of the restriction enzyme or enzymes used in the first step, said fragments also being separated by size, and a third step in which is compared the size of the fragments hybridizing with said probe(s) in the biological specimen and in the test individual, it being understood that there is a presumption that the biological specimen comes from the test individual when the size of the fragments hybridizing with said probe(s) is identical.

It can then be concluded that the biological specimen comes from the tested individual when a sufficiently representative number of fragments hybridizing with probes obtained according to the invention have the same size.

The term "biological specimen" here designates any specimen from which DNA can be extracted to analyze it according to the process described above. This may in particular be a fragment of skin, saliva, sperm, etc.

The process described above also allows verification, in a similar manner, of whether the cells present in a biological specimen actually come from a given cell line.

The following examples illustrate the invention.

EXAMPLE 1

Process of Selecting Probes Capable of Detecting VNTRs a) Preparation of Probes

A cosmid genome bank sold under the name "HL 1145y" by the Clontech Company was used, having as a vector the pWE 15 cosmid, from which a suspension is made at a dilution such that, after smearing on a solid LB-agar culture medium and culturing for 18 hours at 37° C., isolated colonies consisting of a single clone can be obtained.

A fraction of each clone is then inoculated into one well of a 96-well plate, containing a culture medium of the "Terrific Broth" (TB) type (Sambrook, Fritsch, Maniatis, *Molecular Cloning, A Laboratory Manual*, Cold Spring Harbor Laboratory Press, 1989) and left to incubate overnight at 37° C. A replica of the microplate is then made onto a membrane sold under the name "Hybond N+" by the Amersham Company according to the method described by the manufacturer. The membrane thus obtained is placed on a TB culture medium containing approximately 80 μl ampicillin, left to stand overnight at 37° C., then fixed. A volume of 50% glycerol is then added to each well in the plate, then the plates are frozen and stored at −80° C.

In parallel, a 2 ml miniculture is made in a TB medium from one fraction of each colony. These minicultures are left to incubate for 20 hours at 37° C. under agitation.

Groups are then produced by mixing 24 minicultures corresponding to clones inoculated on a given multi-well plate. Cosmidic DNA is extracted for each group by conventional methods.

For each group, the cosmidic DNA extracted is resuspended in 300 μl of 10 mM Tris pH 7.5 1 mM EDTA (TE). From each group, three aliquot fractions of 50 μl are then taken, to which the following pairs of restriction endonucleases (sold by the Appligène Company) are added, respectively:

Alu I and Hae III,
Alu I and Hinf I,
Hinf I and Hae III, each enzyme being at a concentration of approximately 20 units for a total volume completed to 10 μl.

After incubating overnight at 37° C., the hydrolyzed DNA is precipitated in ethanol, separated, then resuspended in 5 μl of TE.

The samples, as well as the size markers, are deposited on a 1% agarose horizontal gel. The fragments are caused to migrate by electrophoresis at approximately 12 V/cm in TAE 1× buffer (Sambrook, Fritsch, Maniatis, *Molecular Cloning, A Laboratory Manual*, Cold Spring Harbor Laboratory Press, 1989). The gel is then developed with ethidium bromide.

For each group and for each hydrolyzate, fragments are cut out from the gel and recovered by centrifuging.

From the approximately 10 to 20 μl of DNA suspension thus recovered, 2 μl are removed and labeled with dCTP ($^{32}$P) by the method described by Feinberg and Volgelstein (*Anal. Biochem.*, 132, 6–13, 1983) using the kit sold by the Boehringer Company.

A set of labeled probes is obtained in this way.

Other sets of labeled probes were obtained in analogous manner from the human genome bank sold under the reference number "951202" by the Stratagene Cloning System Company, also using the pWE 15 cosmid vector, and starting from a human genome bank made in the Supercos I vector of reference number "961200" with the encapsidation lysate known as "Gigapack II" sold by the Stratagene Cloning System Company.

b) The Preparation of DNA Fragment Sets From Tested Individuals (Blots)

DNA from two unrelated individuals is used.

As described above, enzymatic hydrolysis is performed on each DNA sample.

Using the process described above, the fragments obtained are then separated and denatured with 0.4N sodium hydroxide, then the separated single-stranded fragments are transferred to a membrane sold under the name "Hybond N+" by the Amersham Company.

c) Hybridization

Hybridizations by Southern blot transfer were carried out at 65° C. in the manner described by Vergnaud et al., *Electrophoresis*, 12, 134–140 (1991).

The blots obtained for each individual are hybridized with each probe obtained above.

In parallel, with each probe, a replica of the multi-well plate corresponding to the set of probes used is hybridized.

The blots and replicas are then washed and a film of the Kodak XAR 5 type is exposed at −80° C. using amplifier screens.

When the blots and replicas are washed under medium-stringency conditions ($[Na^+]=0.015M$), the exposure time is a few hours up to 12 hours.

When the blots and replicas are washed under medium-stringency conditions, then rewashed under high-stringency conditions ($[Na^+]=0.015M$), the exposure time may be longer, for example 72 hours.

Thus, photographic representations of the hybridizations obtained are produced.

d) Analysis of Hybridization Profiles Obtained

The hybridization profiles obtained are compared with those obtained for the same individual with known probes. When these profiles differ, the probe evidenced is deemed to be new.

If moreover, from one and the same probe obtained by the process, different hybridization profiles are obtained for the two individuals, it may be concluded that the probe used detects a VNTR, with no need for additional confirmation.

Then, on the replica of the multi-well plate, identification is made of the well having strong hybridization with the probe used for both blots, namely the wells containing the clone having one of its DNA strands matching said probe.

Thus, in the corresponding well of the multi-well plate, a clone allowing said probe to be prepared once again becomes available.

Results

From approximately 5,000 clones from a commercial human genome cosmid bank, analyzed by the process described above, approximately 50 new probes detecting new human VNTRs were isolated.

Of these new probes, five were designated as follows: "CEB88", "CEB41", "CEB42", "CEB49", and "CEB69."

The corresponding cultures were frozen, then deposited with the CNCM under numbers I-1343, I-1344, I-1345, I-1346, and I-1347, respectively.

The proportion of cosmids containing at least one VNTR for a complete human genome cosmid bank is estimated to be 2 or 3%. The process described here allowed isolation of one VNTR for one hundred cosmids. Hence this process allows identification of at least 30 to 50% of the VNTR sequences present in the bank.

Using the process described above, VNTRs from different genomes were isolated. Thus, the validity of the process described was tested not only in man but also in rats. For example in rats, approximately 10,000 clones were analyzed and about a hundred VNTRs were isolated.

What is claimed is:

1. A probe including at least forty nucleotides of a human genome sequence in a cloning site of a vector in culture selected from the group consisting of cultures deposited with the CNCM under reference numbers I-1343, I-1344, I-1345, I-1346, and I-1347, said probe being capable of hybridizing to a VNTR region.

2. A process of consanguinity testing, comprising comparing a first hybridization profile, generated by hybridizing a probe of claim 1 to a first set of DNA restriction fragments derived from a first individual, to a second hybridization profile, generated by hybridizing said probe to a second set of DNA restriction fragments derived from a second individual.

3. A process of screening for hereditary disease, comprising comparing a first hybridization profile, generated by hybridizing a probe of claim 1 to a first set of DNA restriction fragments derived from a test individual, to a second hybridization profile, generated by hybridizing said probe to a second set of DNA restriction fragments derived from a healthy individual.

4. A process of screening for tumoral disease, comprising comparing a first hybridization profile, generated by hybridizing a probe of claim 1 to a first set of DNA restriction fragments derived from test cells of an individual, to a second hybridization profile, generated by hybridizing said probe to a second set of DNA restriction fragments derived from normal cells of said individual.

5. A process of identifying a biological specimen, comprising comparing a first hybridization profile, generated by hybridizing a probe of claim 1 to a first set of DNA restriction fragments derived from a biological specimen, to a second hybridization profile, generated by hybridizing said probe to a second set of DNA restriction fragments derived from a DNA-containing test source.

6. A process of consanguinity testing between two individuals, comprising:
   (1) placing at least one labeled probe of claim 1 in contact, under hybridization conditions, with a first set of restriction fragments obtained by: (a) hydrolyzing a first sample of genomic DNA from a first individual with at least one restriction enzyme that cuts at an essentially constant distance from a site recognized by said restriction enzyme; and (b) separating restriction fragments thus obtained by size;
   (2) placing at least one labeled probe of claim 1 in contact, under hybridization conditions, with a second set of restriction fragments obtained by: (a) hydrolyzing a second sample of genomic DNA from a second individual, whose consanguinity with said first individual is to be determined, with said restriction enzyme of step (1)(a); and (b) separating restriction fragments thus obtained by size; and
   (3) comparing sizes of restriction fragments from said first individual and restriction fragments from said second individual that hybridize with said at least one labeled probe, wherein consanguinity is presumed when the sizes of said restriction fragments hybridizing with said labeled probe are identical for said first and second individuals.

7. A process of screening for tumoral diseases, comprising:
   (1) placing at least one labeled probe of claim 1 in contact, under hybridization conditions, with a first set of restriction fragments obtained by: (a) hydrolyzing a first sample of genomic DNA from test cells of an individual with at least one restriction enzyme that cuts at an essentially constant distance from a site recognized by said restriction enzyme; and (b) separating restriction fragments thus obtained by size;
   (2) placing at least one labeled probe of claim 1 in contact, under hybridization conditions, with a second set of restriction fragments obtained by: (a) hydrolyzing a second sample of genomic DNA from normal cells of the same individual, with said restriction enzyme of step (1)(a); and (b) separating restriction fragments thus obtained by size; and
   (3) comparing numbers and sizes of restriction fragments from said test cells and restriction fragments from said normal cells that hybridize with said at least one labeled probe, wherein tumoral disease is diagnosed when the number or sizes of said restriction fragments hybridizing with said labeled probe are identical for said test and normal cells.

8. A process of screening for hereditary diseases, comprising:
   (1) placing at least one labeled probe of claim 1 in contact, under hybridization conditions, with a first set of restriction fragments obtained by: (a) hydrolyzing a first sample of genomic DNA from a test individual with at least one restriction enzyme that cuts at an essentially constant distance from a site recognized by said restriction enzyme; and (b) separating restriction fragments thus obtained by size;
   (2) placing at least one labeled probe of claim 1 in contact, under hybridization conditions, with a second set of restriction fragments obtained by: (a) hydrolyzing a second sample of genomic DNA from a healthy individual, with said restriction enzyme of step (1)(a); and (b) separating restriction fragments thus obtained by size; and
   (3) comparing numbers of restriction fragments from said test individual and restriction fragments from said healthy individual that hybridize with said at least one labeled probe, wherein predisposition to hereditary disease is diagnosed when the numbers of said restriction fragments hybridizing with said labeled probe differ for said test and normal individuals.

9. A process of identifying a biological specimen containing genomic DNA by comparison with genomic DNA from a test individual, comprising:
   (1) placing at least one labeled probe of claim 1 in contact, under hybridization conditions, with a first set of restriction fragments obtained by: (a) hydrolyzing a first sample of genomic DNA from said biological specimen with at least one restriction enzyme that cuts at an essentially constant distance from a site recognized by said restriction enzyme; and (b) separating restriction fragments thus obtained by size;
   (2) placing at least one labeled probe of claim 1 in contact, under hybridization conditions, with a second set of restriction fragments obtained by: (a) hydrolyzing a second sample of genomic DNA from said test individual, with said restriction enzyme of step (1)(a); and (b) separating restriction fragments thus obtained by size; and
   (3) comparing sizes of restriction fragments from said biological specimen and restriction fragments from said test individual that hybridize with said at least one labeled probe, wherein said biological specimen is presumed to come from said test individual when the sizes of the fragments hybridizing with said restriction fragments hybridizing with said labeled probe differ for said biological specimen and said test individual.

10. The probe according to claim 1, wherein said culture is deposited with the CNCM under the reference number I-1343.

11. The probe according to claim 1, wherein said culture is deposited with the CNCM under the reference number I-1344.

12. The probe according to claim 1, wherein said culture is deposited with the CNCM under the reference number I-1345.

13. The probe according to claim 1, wherein said culture is deposited with the CNCM under the reference number I-1346.

14. The probe according to claim 1, wherein said culture is deposited with the CNCM under the reference number I-1347.

* * * * *